United States Patent
Machado et al.

(10) Patent No.: US 7,725,196 B2
(45) Date of Patent: May 25, 2010

(54) CORPUS CALLOSUM NEUROMODULATION ASSEMBLY

(75) Inventors: Andre Machado, Sao Paulo (BR); Ali R. Rezai, Bratenahl, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1006 days.

(21) Appl. No.: 11/121,057

(22) Filed: May 4, 2005

(65) Prior Publication Data

US 2005/0288760 A1 Dec. 29, 2005

Related U.S. Application Data

(60) Provisional application No. 60/608,417, filed on Sep. 10, 2004, provisional application No. 60/608,418, filed on Sep. 10, 2004, provisional application No. 60/567,441, filed on May 4, 2004.

(51) Int. Cl.
*A61N 1/05* (2006.01)

(52) U.S. Cl. .................... 607/116; 600/378; 607/45; 607/46

(58) Field of Classification Search ................ 607/116; 600/378
See application file for complete search history.

(56) References Cited

U.S. PATENT DOCUMENTS

| | | | | |
|---|---|---|---|---|
| 3,999,555 A * | 12/1976 | Person | ........................ | 607/130 |
| 4,144,889 A | 3/1979 | Tyers et al. | | |
| 4,177,818 A * | 12/1979 | De Pedro | ..................... | 607/130 |
| 4,735,208 A * | 4/1988 | Wyler et al. | ................... | 600/377 |
| 4,765,341 A * | 8/1988 | Mower et al. | ................ | 607/116 |
| 5,255,693 A | 10/1993 | Dutcher | | |
| 5,897,583 A * | 4/1999 | Meyer et al. | ................. | 607/116 |
| 6,205,361 B1 | 3/2001 | Kuzma | | |
| 6,600,956 B2 * | 7/2003 | Maschino et al. | ........... | 607/118 |
| 6,606,523 B1 | 8/2003 | Jenkins | | |
| 7,054,692 B1 * | 5/2006 | Whitehurst et al. | .......... | 607/149 |
| 2002/0183817 A1 | 12/2002 | Van Venrooij et al. | | |
| 2005/0049649 A1 | 3/2005 | Luders et al. | | |
| 2007/0027514 A1 * | 2/2007 | Gerber | ....................... | 607/116 |

FOREIGN PATENT DOCUMENTS

| | | |
|---|---|---|
| EP | 1048320 | 11/2000 |
| EP | 1166819 | 1/2002 |
| WO | WO 98/48880 | 11/1998 |
| WO | 02072192 | 2/2002 |
| WO | WO 02/26314 | 4/2002 |
| WO | WO 02/28473 | 4/2002 |

OTHER PUBLICATIONS

International Search Report, International Application No. PCT/US05/15425, dated Nov. 22, 2006, (2 pgs.).
Supplemental European Search Report dated Mar. 18, 2008 for EP 05742697.5 based on International Patent Application PCT/US2005/015425.
Aug. 28, 2009 Office Action issued in counterpart European Patent Application No. 05742697.5.

* cited by examiner

*Primary Examiner*—Kennedy J Schaetzle
(74) *Attorney, Agent, or Firm*—Kenyon & Kenyon LLP

(57) ABSTRACT

Neuromodulation assemblies with lead bodies having curvatures that mimic the curvatures of the splenium, trunk, genu, or rostrum of the corpus callosum. Methods of stimulating the corpus callosum and methods of securing an electrical lead in the brain are also provided.

27 Claims, 13 Drawing Sheets

CORPUS CALLOSUM NEUROMODULATION ASSEMBLY

CROSS-REFERENCE TO RELATED APPLICATIONS

The present application claims priority to U.S. Provisional Application Nos. 60/608,417, filed on Sep. 10, 2004, 60/608,418, filed on Sep. 10, 2004 and 60/567,441, filed on May 4, 2004.

FIELD OF THE INVENTION

The present invention is directed to a neuromodulation assembly for stimulating neural tissue.

BACKGROUND OF THE INVENTION

Electrical stimulation of neural tissue is becoming an increasingly preferred form of therapy for various neurological conditions and disorders. Such therapy provides distinct advantages over surgical lesioning techniques since electrical stimulation is a reversible and adjustable procedure that provides continuous benefits as the patient's disease progresses and the patient's symptoms evolve.

Currently, electrical stimulation of peripheral nerves and the spinal cord is approved for treatment of neuropathic pain. With respect to deep brain targets, electrical stimulation of the subthalamic nucleus and the globus pallidus interna is approved for treatment of Parkinson's disease and electrical stimulation of the ventral intermediate nucleus is approved for treatment of essential tremor.

There remains a need for further forms of neuromodulation and devices to accomplish the same.

SUMMARY OF THE INVENTION

In an embodiment, the present invention provides a neuromodulation assembly comprising a lead body having a top surface and a bottom surface. The lead body has a curvature that mimics the curvature of the trunk, the genu, the splenium, or the rostrum of the corpus callosum in an operative position of the lead body. The neuromodulation assembly further comprises an electrical contact exposed at the bottom surface and not the top surface of the lead body, a conductor coupled to the electrical contact and extending from the lead body, and an anchor disposed on the conductor.

In an embodiment, the present invention provides a neuromodulation assembly comprising a lead body having a top surface and a bottom surface. The lead body has a curvature that mimics the curvature of the trunk, the genu, the splenium, or the rostrum of the corpus callosum in an operative position of the lead body. The neuromodulation assembly further comprises an electrical contact exposed at the bottom surface and not the top surface of the lead body, a conductor coupled to the electrical contact and extending from the lead body, an accessory strand extending from the lead body, and an anchor disposed on the accessory strand.

In an embodiment, the present invention provides a method of stimulating the corpus callosum comprising placing an electrical lead having an electrode disposed thereon in communication with a corpus callosum and activating the electrode to apply an electrical signal to the corpus callosum to stimulate the corpus callosum.

In an embodiment, the present invention provides a method of securing an electrical lead comprising a lead body having an electrode disposed thereon. The method comprises anchoring the lead to the dura mater of the brain.

BRIEF DESCRIPTION OF THE INVENTION

The present invention will become more fully understood from the detailed description given hereinbelow and the accompanying drawings which are given by way of illustration only and wherein.

DETAILED DESCRIPTION OF THE INVENTION

Figure 1:
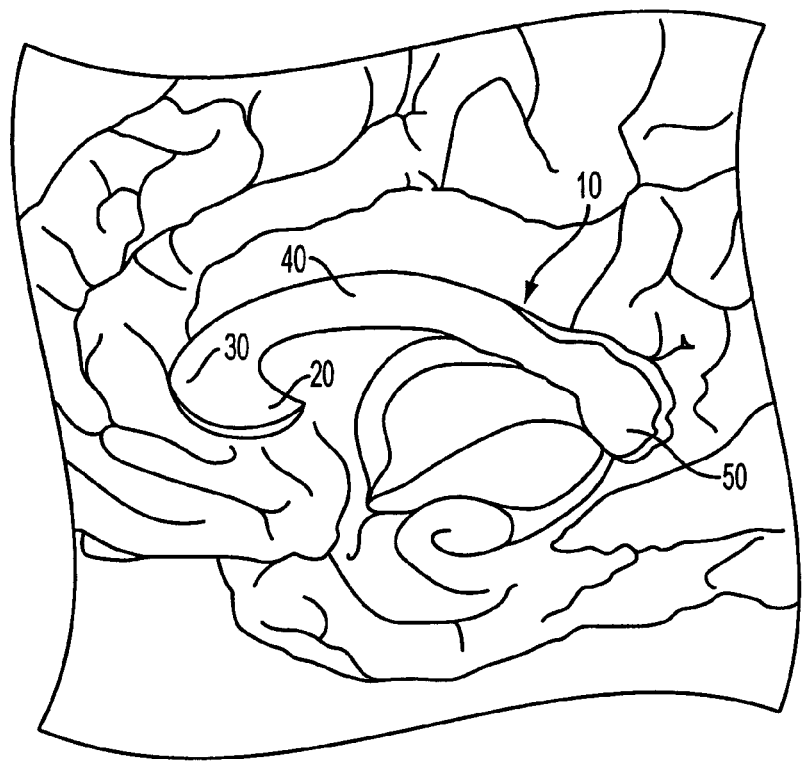
FIG. 1 depicts a sagittal section of the brain showing the corpus callosum.

The present invention provides embodiments of electrical lead assemblies for neuromodulation of the corpus callosum. Referring to FIG. 1 and as is known to one of skill in the art, the corpus callosum 10 is located between the hemispheres in the floor of the interhemispheric fissure and the roof of the lateral ventricles. The corpus callosum 10 has two anterior parts, the rostrum 20 and the genu 30, a central part, the trunk 40 (also referred to as the body of the corpus callosum), and a posterior part, the splenium 50. The anterior parts 20 and 30 are situated in the midline deep to the upper part of the inferior frontal gyrus. As illustrated in FIG. 1, the genu 30 blends below into the rostrum 20, which is thin and tapered. Rostrum 20 is continuous downward in front of the anterior commissure, with the lamina terminalis. The curved genu 30 wraps around and forms the anterior wall and adjacent part of the roof of the frontal horn as it extends obliquely forward and lateral to connect the frontal lobes. As illustrated in FIG. 1, the genu 30 blends posteriorly into the trunk 40, located above the body of the lateral ventricle. The genu 30 and the trunk 40 of the corpus callosum 10 form the roof of both the frontal horn and the body of the lateral ventricle. The splenium 50 is situated deep to the supramarginal gyrus and the lower third of the pre-and postcentral gyri. As illustrated in FIG. 1, the splenium 50 is the thick rounded posterior end of the corpus callosum 10 and is situated dorsal to the pineal body and the upper part of the medial wall of the atrium. The splenium 50 contains a fiber tract, the forceps major, which forms a prominence, called the bulb, in the upper part of the medial wall of the atrium and occipital horn as it extends posteriorly to connect the occipital lobes. The cingulate gyrus surrounds and is separated from the corpus callosum 10 by the callosal sulcus. Further description of the corpus callosum 10 are described in Rhoton, Albert, L. Jr. M.D. The Lateral and Third Ventricles. Neurosurgery 51(4) SUPPLEMENT 1: S1-207-271 (October 2002); Rhoton, Albert L. Jr. M.D. The Cerebrum. Neurosurgery. 51(4) SUPPLEMENT 1:S1-1-52 (October 2002), both of which are incorporated by reference herein.

Figure 2:
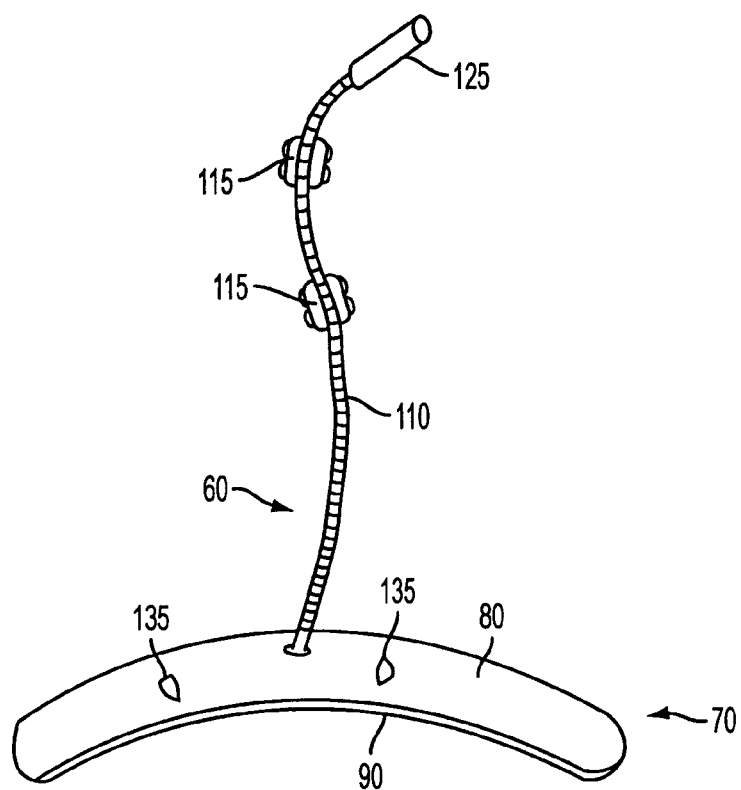
FIG. 2 is a perspective view of an embodiment of a neuromodulation assembly according to the present invention.
Figure 3:
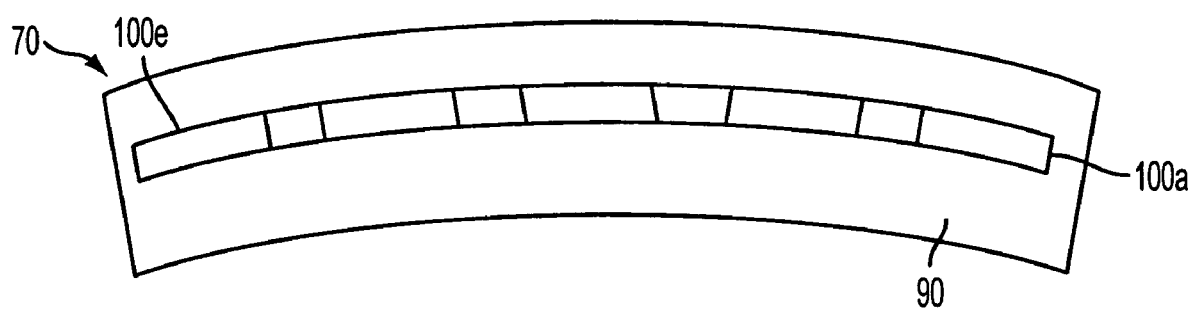
FIG. 3 is a bottom view of a neuromodulation assembly according to the present invention.
Figure 4:
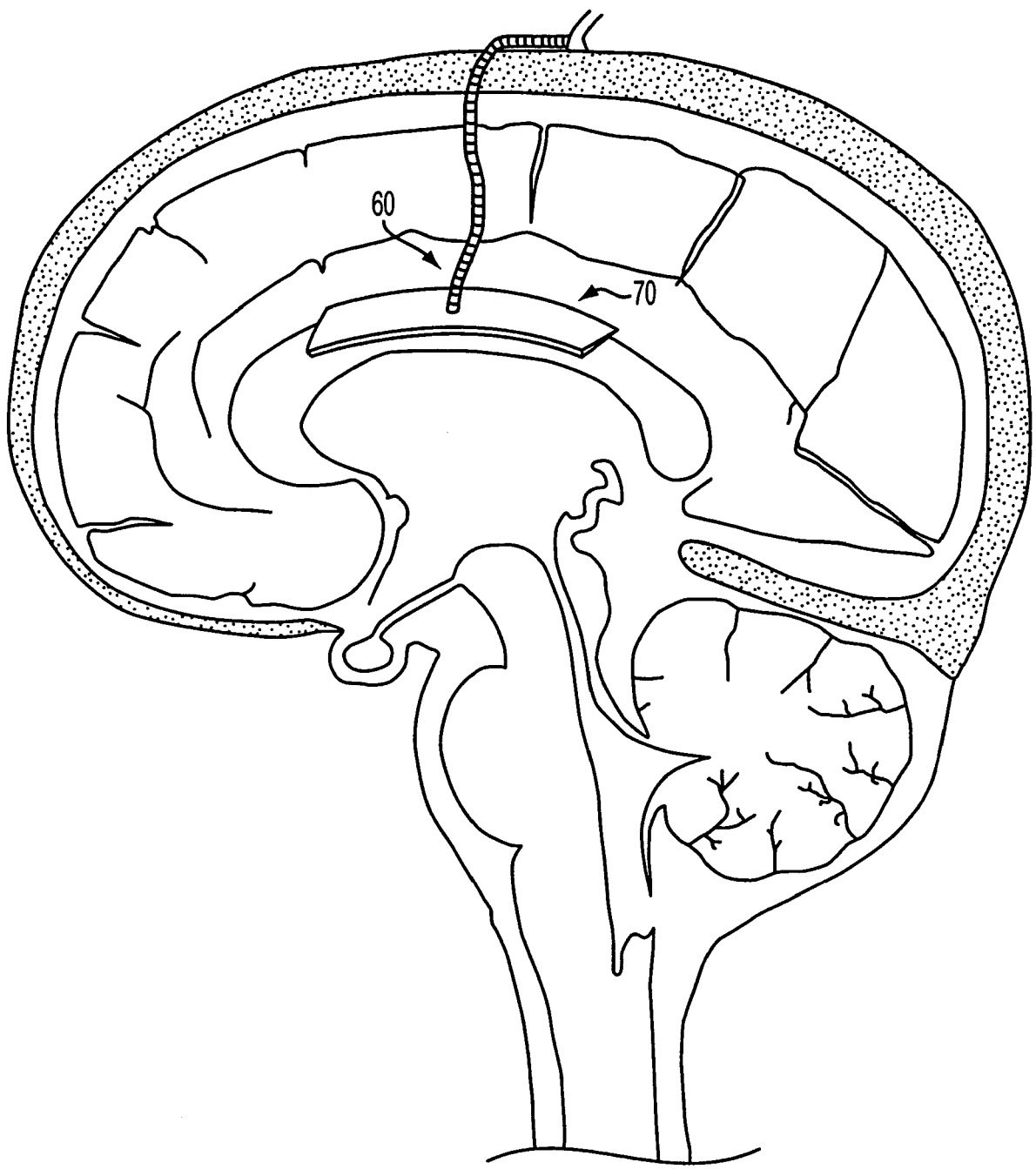
FIG. 4 depicts an embodiment of a neuromodulation assembly according to the present invention positioned on the trunk of the corpus callosum.

Referring to FIGS. 2-7, embodiments of the present invention provide a neuromodulation assembly 60 comprising a lead body 70 having a top surface 80 and a bottom surface 90. As used herein, the terms "top," "bottom," and "under-surface" are defined relative to the operative position of lead body 70 of neuromodulation assembly 60. As used herein, the term "operative position" refers to the position of lead body 70 when lead body 70 is positioned on the target region of the corpus callosum 10 and neuromodulation assembly 60 is ready to be activated to initiate therapy to the target region of the corpus callosum 10. As referred to herein, the "target region of the corpus callosum" is the trunk, genu, rostrum, or splenium of the corpus callosum. Referring to FIG. 3, an electrical contact 100 from an electrode, and preferably a plurality (i.e. more than one) of electrical contacts 100 from one or from a plurality of respective electrodes, is exposed at the bottom surface 90 of lead body 70. Top surface 80, however, is insulated such that no electrical contact is exposed at top surface 80. Referring again to FIG. 2, neuromodulation assembly 60 further comprises a conductor 110 that is coupled to an electrode having an electrical contact 100. Conductor 110 extends from lead body 70 to directly or indirectly be connected to an implantable pulse generator. To this end, conductor 110 of neuromodulation assembly 60 may further comprise a connector 125 to connect to a mating connector of an extension lead, which in turn is connectable to an implantable pulse generator. Neuromodulation assembly 60 further comprises an anchor 115, and preferably a plurality of anchors 115, which in the embodiment depicted in FIG. 2, is disposed on conductor 110.

Figure 5:
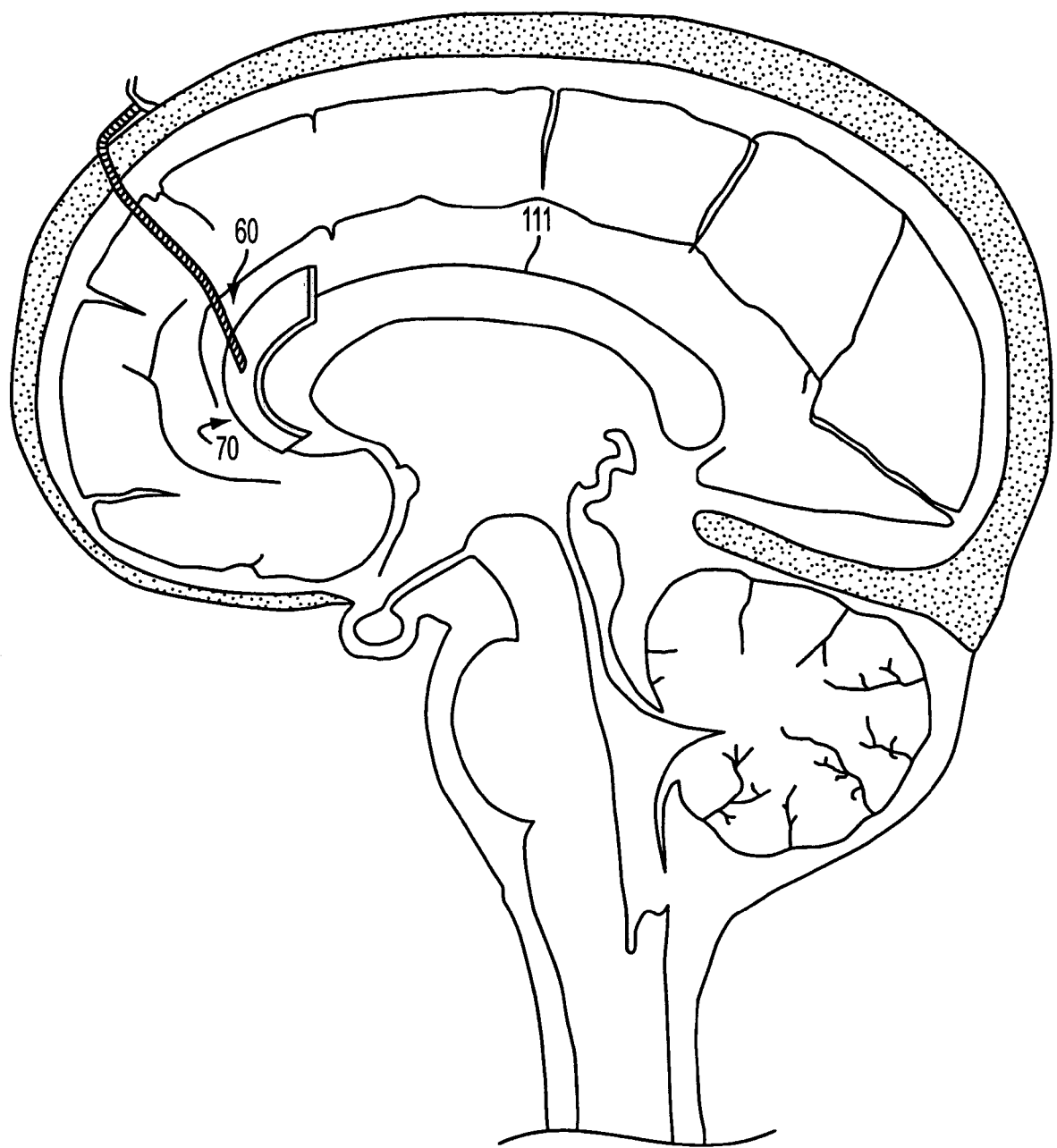
FIG. 5 depicts an embodiment of a neuromodulation assembly according to the present invention positioned on the genu of the corpus callosum.
Figure 6:
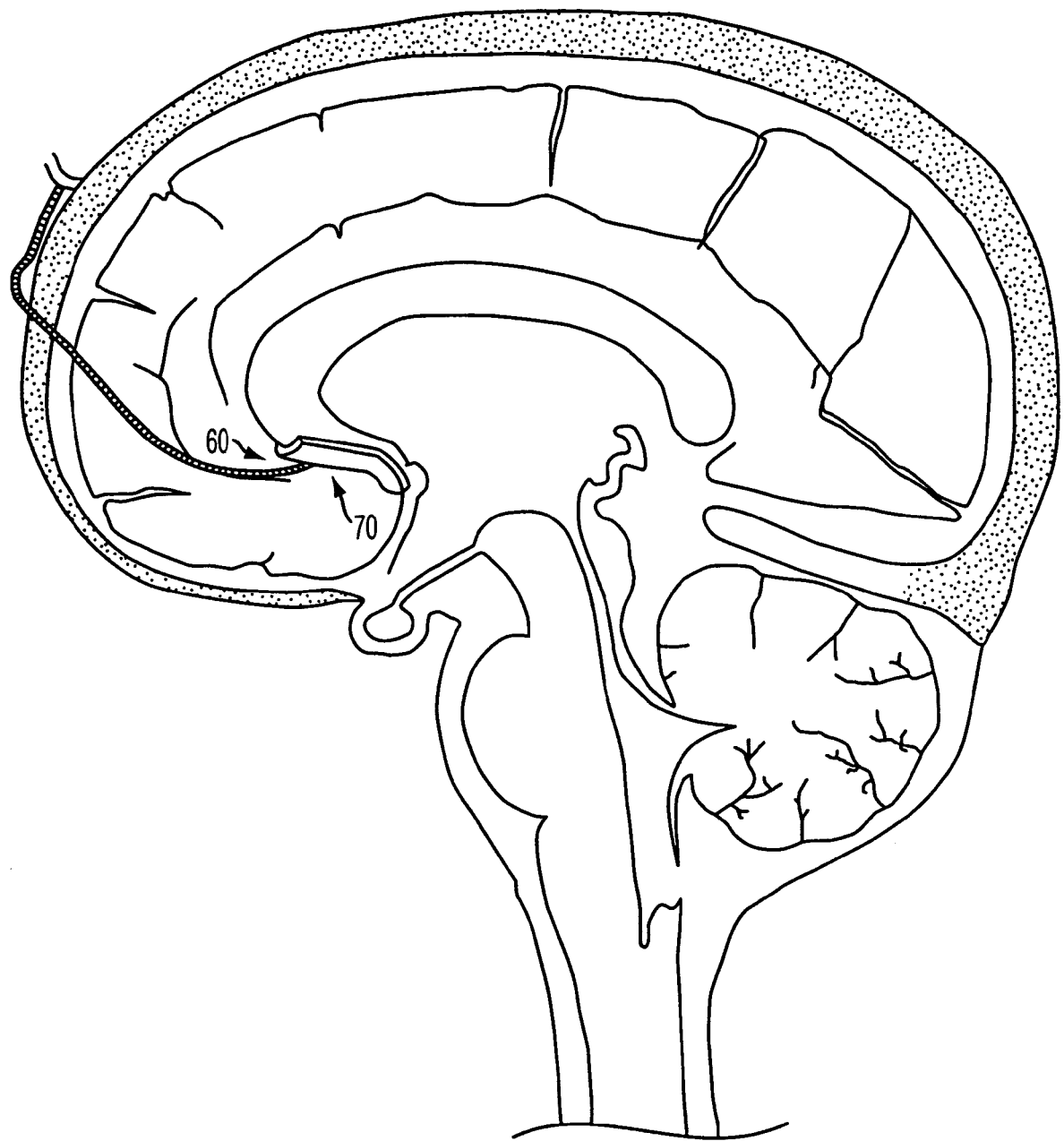
FIG. 6 depicts an embodiment of a neuromodulation assembly according to the present invention positioned on the rostrum of the corpus callosum.
Figure 7:
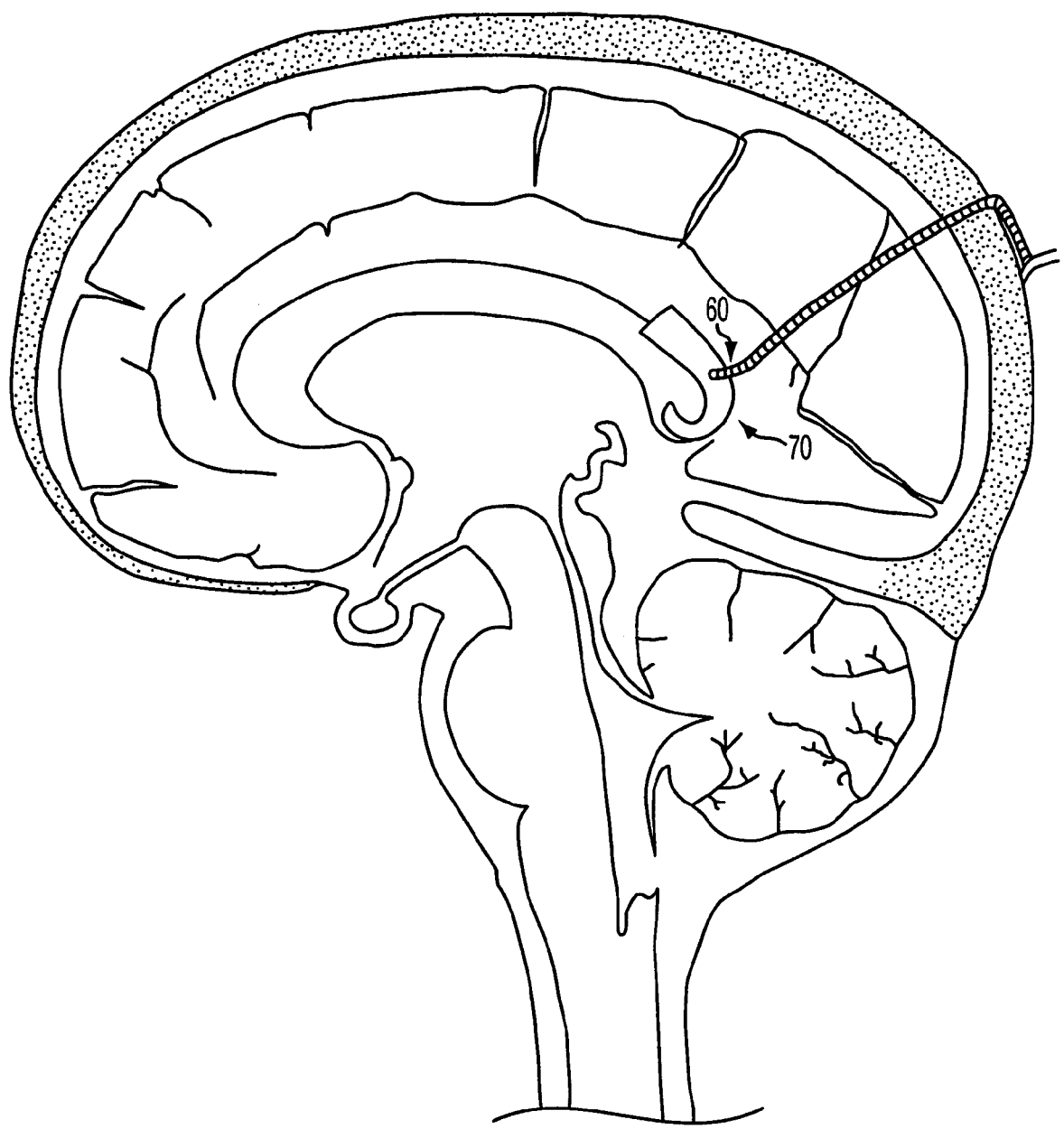
FIG. 7 depicts an embodiment of a neuromodulation assembly according to the present invention positioned on the splenium of the corpus callosum.

The present invention provides embodiments of lead body 70 that each have a curvature that mimics the curvature of a target region of the corpus callosum 10. Specifically, referring to FIG. 4, in an embodiment, lead body 70 has a curvature that mimics the curvature of the trunk 40 of the corpus callosum 10 in an operative position of lead body 70. Referring to FIG. 2, in such an embodiment, conductor 110 preferably extends from substantially the center of lead body 70. Referring to FIG. 5, in another embodiment, lead body 70 has a curvature that mimics the curvature of the genu 30 of the corpus callosum 10 in an operative position of lead body 70. Referring to FIG. 6, in another embodiment, lead body 70 has a curvature that mimics the curvature of the rostrum 20 of the corpus callosum 10 in an operative position of lead body 70. Referring to FIG. 7, in yet another embodiment, lead body 70 has a curvature that mimics the curvature of the splenium 50 of the corpus callosum 10 in an operative position of lead body 70. In the embodiments depicted in FIGS. 5-7, conductor 110 preferably extends from one of the side ends of lead body 70.

The trunk 40, the genu 30, the rostrum 20, and the splenium 50 of the corpus callosum 10 are described above and are well-defined neuroanatomical sites. Therefore, the curvatures of these regions are well known to one of ordinary skill in the art. Because the curvatures of lead bodies 70 of these embodiments of the present invention mimic the curvatures of these regions, such curvatures of lead bodies 70 will also be well-understood by one of skill in the art. In general, in embodiments where lead body 70 mimics the curvature of the trunk 40 or the rostrum 20, lead body 70 has a cambered configuration. In embodiments where lead body 70 mimics the curvature of the splenium 50, lead body 70 has a generally J-shaped configuration. As used herein, the phrase "mimics the curvature" encompasses configurations of lead body 70 that not only conform to the general curvature of a target region of the corpus callosum 10 but also follow the general curvature of the respective target region of the corpus callosum 10 such that lead body 70 grasps such region to allow for a more secure fit of the lead body 70 on such region.

Figure 9:
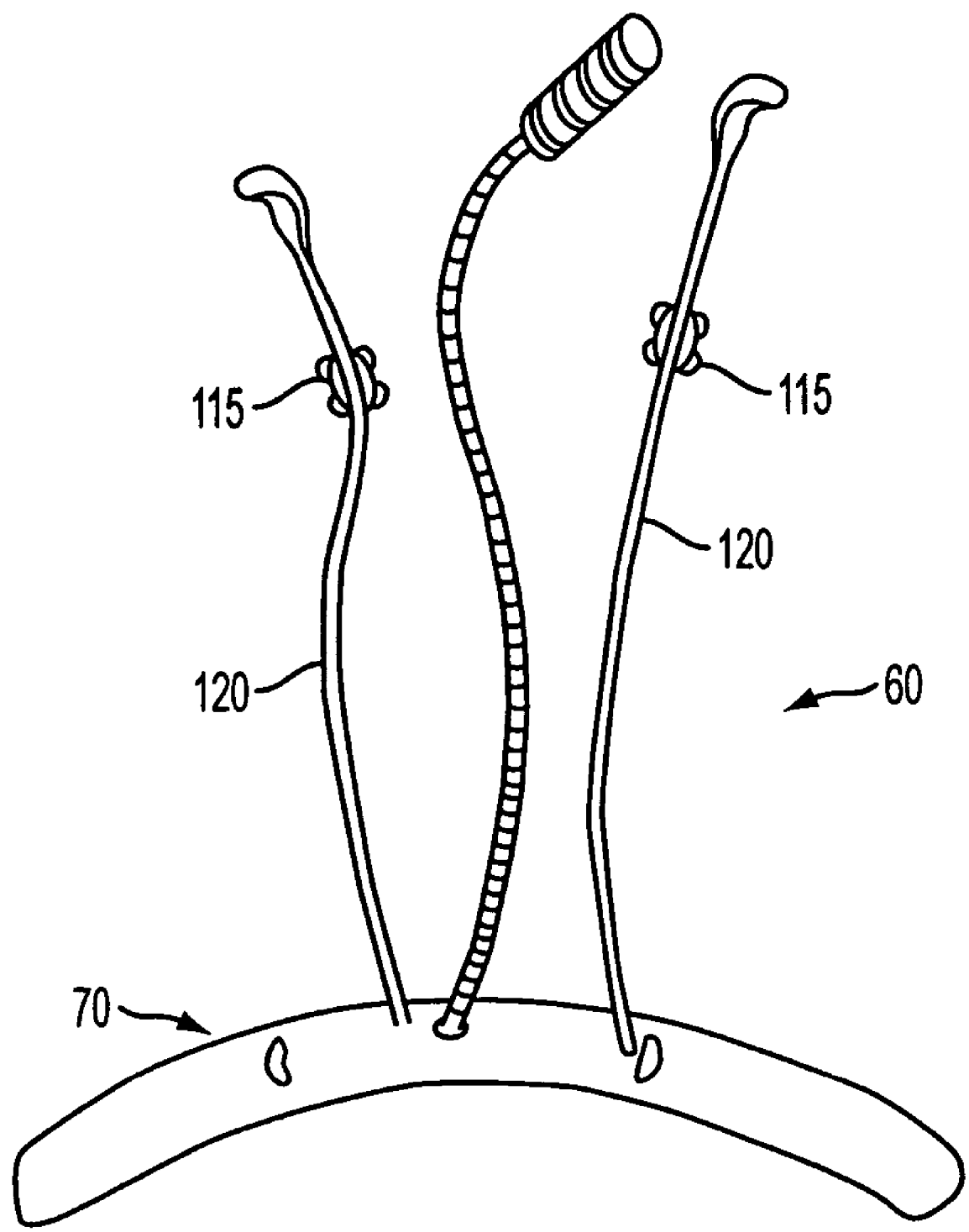
FIG. 9 depicts an alternative embodiment of a neuromodulation assembly according to the present invention.

With respect to specific details of neuromodulation assembly 60, as described above, neuromodulation assembly 60 further comprises an anchor 115 for securing lead body 70 in the brain. As illustrated in FIG. 2, in an embodiment, anchor(s) 115 is disposed on conductor 110. Referring to FIG. 9, in an alternative embodiment, neuromodulation assembly 60 comprises an accessory strand 120, or a plurality of accessory strands 120 as specifically illustrated in FIG. 9, which extends from lead body 70 and has an anchor 115 disposed thereon. In the case of a plurality of accessory strands 120, each accessory strand 120 has at least one anchor 115 disposed thereon. In either embodiment, anchor 115 is preferably slidably disposed on conductor 110 or accessory strand 120 so that anchor 115 can be appropriately moved along the longitudinal axis of conductor 110 or accessory strand 120 to be positioned adjacent the desired anchoring site of the brain. Anchor 115 may be any structure known in the art that is suitable for anchoring lead body 70 in the brain. Non-limiting examples of anchor 115 include a tine, hook, suture sleeve, or twist-lock as described in U.S. Pat. No. 5,843,146, which is incorporated by reference herein.

As mentioned above, electrical contacts 100 of electrodes are exposed at the bottom surface 90 of lead body 70. Preferably, such electrodes are adjustably powerable. For example, the pulsing parameters of the electrodes may be adjusted to initiate, stop, increase, or decrease the pole combinations, energy, amplitude, pulse width, waveform shape, frequency, and/or voltage or any other pulsing parameter known to one of skill in the art to adjust the degree of stimulation delivered thereby. In a preferred embodiment, each electrode is selectively powerable such that the pulsing parameters of an electrode can be adjusted independent of the pulsing parameters of another electrode.

Figure 14:
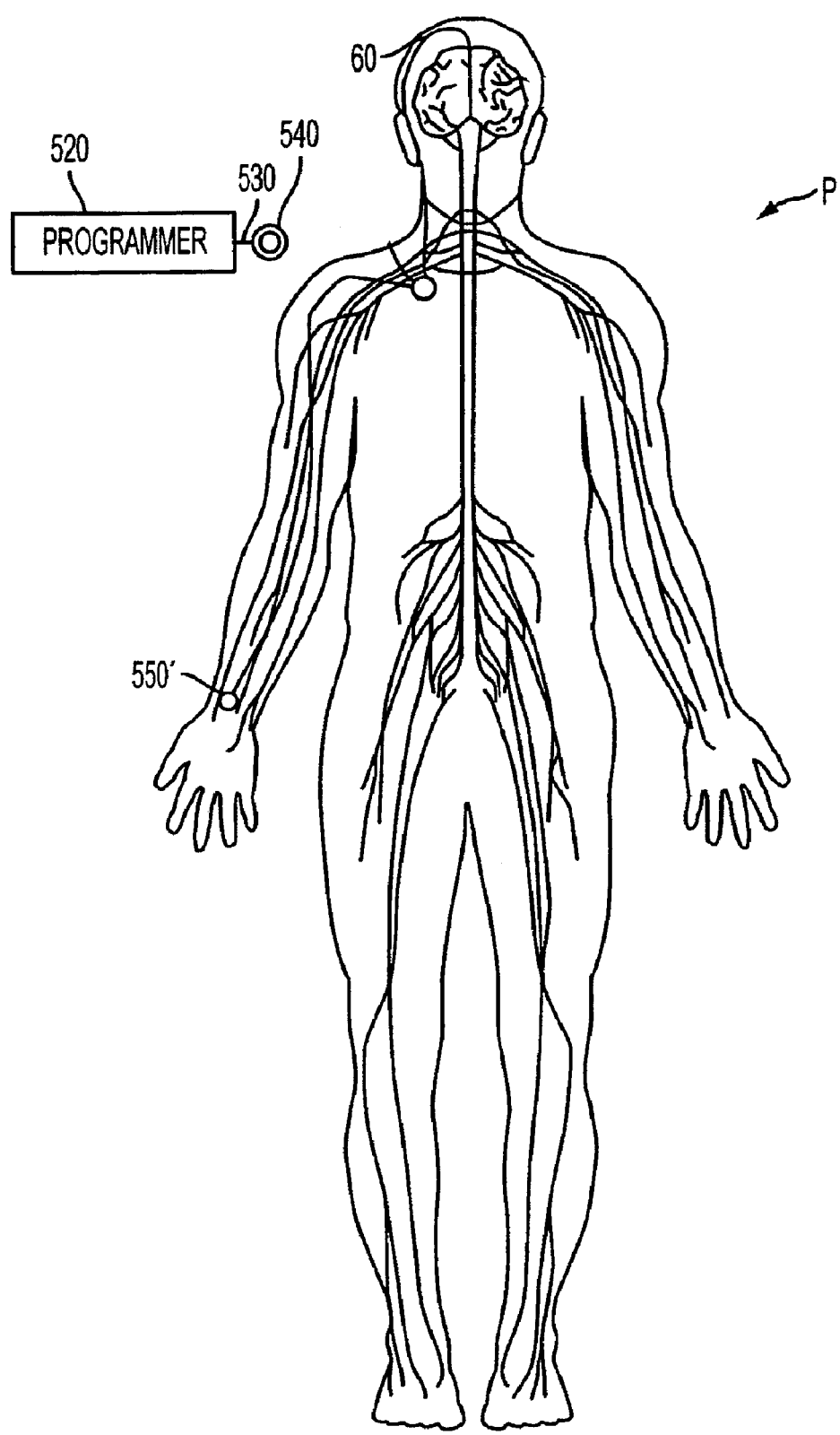
FIG. 14 is a diagrammatic view of a patient in which an embodiment of a neuromodulation assembly has been implanted.

Referring to FIG. 14, the selective powerability over each electrode may be achieved by employing a system including a programmer 520 coupled via a conductor 530 to a telemetry antenna 540. The programmer 520 is capable of sending signals via the telemetry antenna 540 to control the electrical signal delivered to electrodes. Such a system permits the selection of various pulse output options after the neuromodulation assembly 60 is implanted using telemetry communications. The present invention also contemplates radio-frequency systems to selectively power the electrodes.

As will be understood by one of skill in the art, the independent powerability of the electrodes also provides a practitioner with a means of modifying or steering the direction of stimulation as the locus of stimulation can be selectively adjusted to precisely target portions of the target region of the corpus callosum 10 to achieve the desired therapy. For example, with reference to FIG. 3, electrode having electrical contact 100a may be powered to stimulate an area adjacent thereto while the signal to the electrode having electrical contact 100e may be substantially minimized to reduce or stop stimulation to an area adjacent to electrical contact 100e. Because the locus of stimulation can be selectively adjusted and/or steered in this embodiment of neuromodulation assembly 60, specific areas of the target regions of the corpus callosum can be precisely targeted to achieve the desired therapy. Other or additional means of selectively steering electrical stimulation may also be utilized in the present invention, such as the methods described in U.S. Pat. No. 5,713,922, which is incorporated by reference herein.

Figure 8:
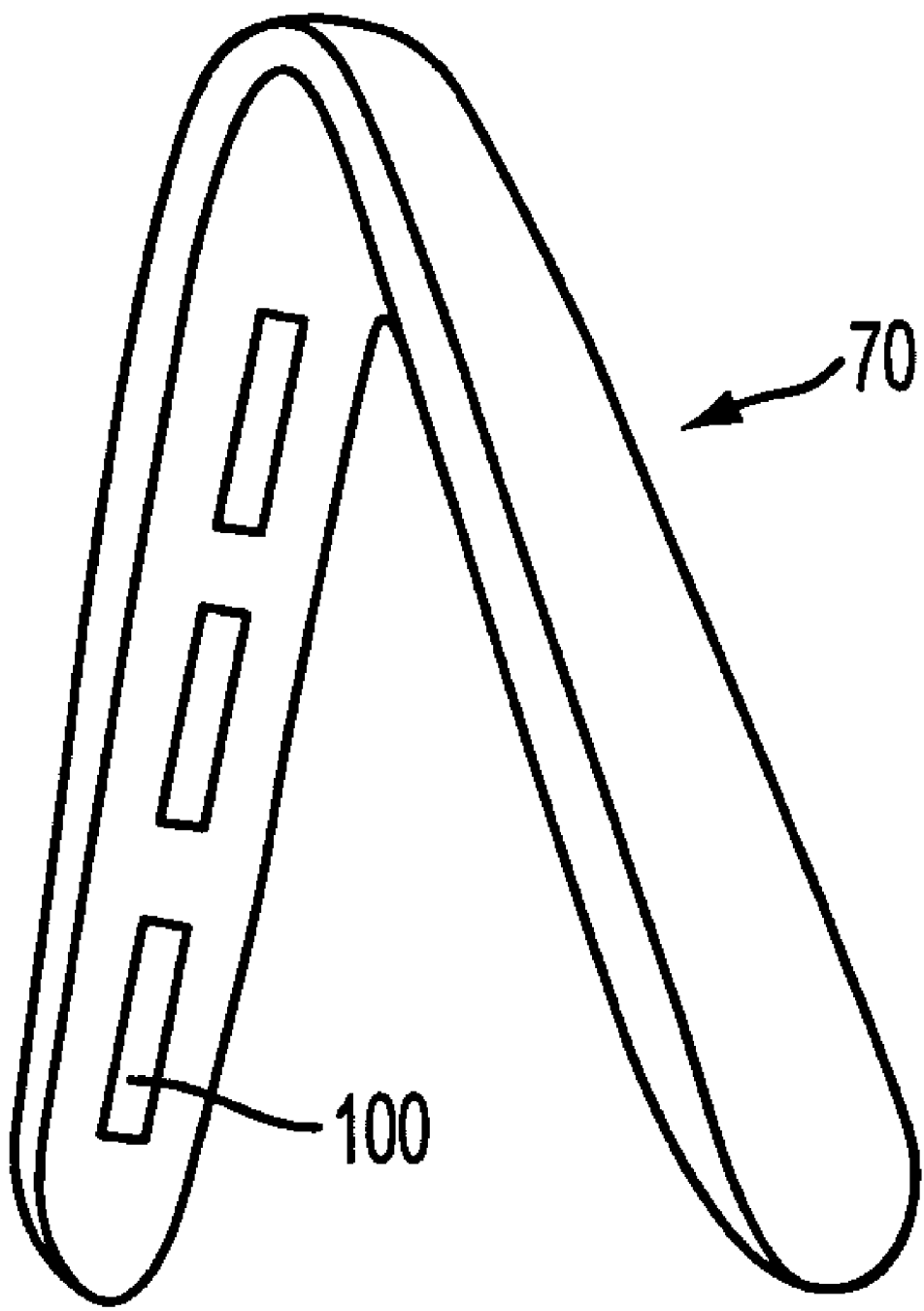
FIG. 8 depicts a lead body of the present invention in a pre-operative position.

In a preferred embodiment, lead body 70 is fabricated from a flexible material that is deformable from a pre-operative position to the operative position and is configured to retain its shape when in the operative position. In a pre-operative position, illustrated in FIG. 8, lead body 70 is folded at an angle sufficient to clear the superficial levels of the brain above the corpus callosum 10, such as the venous complexes and superior sagittal sinus upon entry into the brain. Once lead body 70 reaches the corpus callosum, lead body 70 can unfold and assume the operative position on the trunk, genu, rostrum, or splenium of the corpus callosum. In such embodiments, the flexible material of lead body 70 may comprise, for example, a rubber, a shape memory alloy such as nickel-titanium alloys ("Nitinol") and copper based alloys, or a superelastic material.

Figure 10:
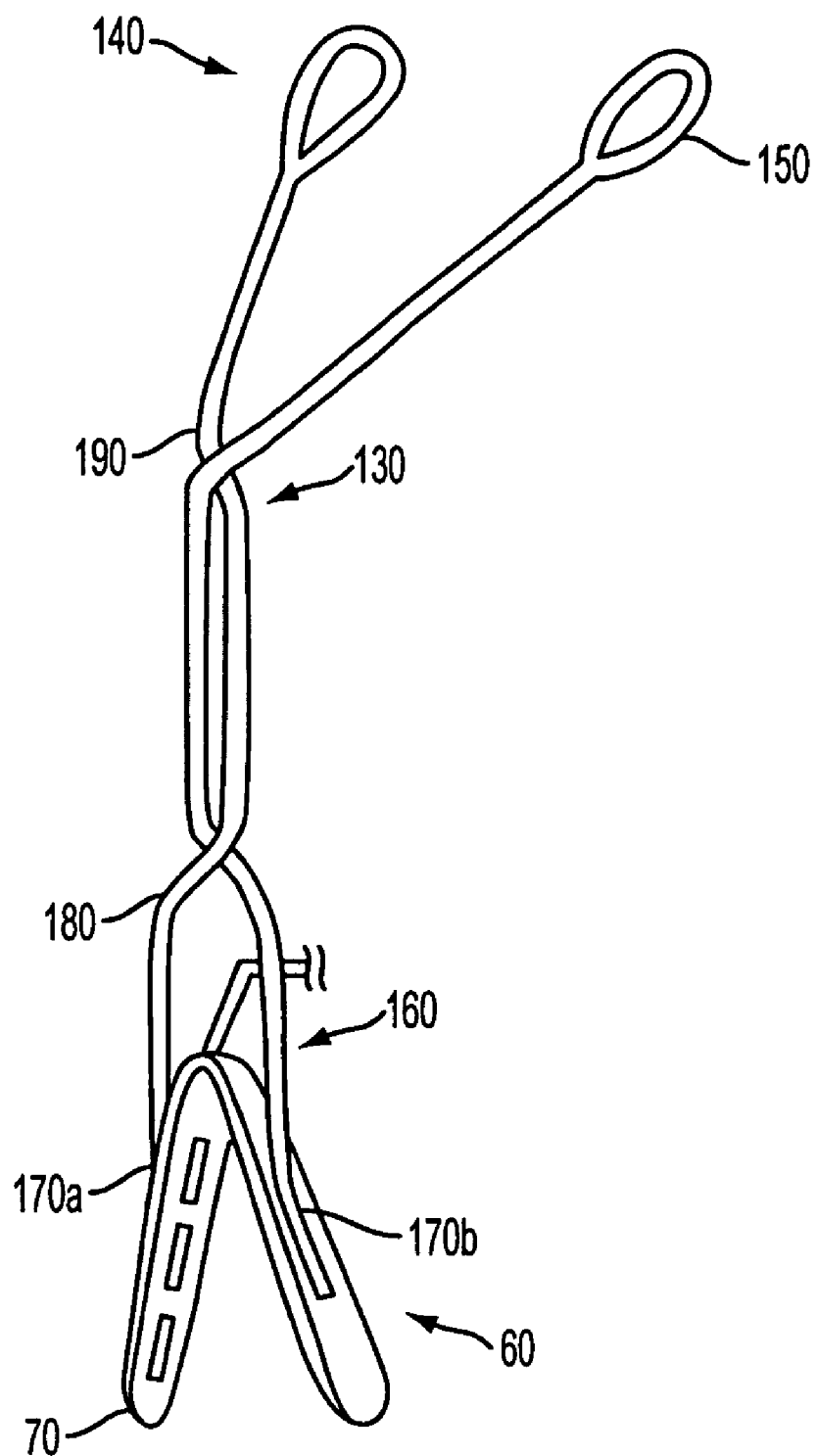
FIG. 10 depicts a neuromodulation kit according to an embodiment of the present invention.

Referring back to FIG. 2, top surface 80 of lead body 70 may comprise a fastener 135 or a plurality of fasteners 135 that cooperates with portions of an installation tool to secure an installation tool to lead body 70. Non-limiting examples of suitable fasteners 135 include a strap, buckle, a groove, a through-hole, or a snap. In general, any fastening mechanism may be used to secure an installation tool to lead body 70 such as, for example, a hook-and eye mechanism, a hook and loop mechanism such as that employed under the tradename VELCRO, clamps, staples, and any type of male-female mating members such as nuts and screws, rivets, and the like. Referring to FIG. 10, in another embodiment, the present invention provides a neuromodulation kit comprising an neuromodulation assembly 60 having a lead body 70 including a pair of fasteners 135 (illustrated in FIG. 2) and an installation tool 130 having a proximal portion 140 comprising a handle 150 and a distal portion 160 comprising a pair of arms 170a and 170b that are connected to one another by a first pivot 180. Arms 170a and 170b have distal ends configured to releasably cooperate with fasteners 135 of lead body 70. In the embodiment depicted in FIG. 10 (and FIG. 2), fasteners 135 are grooves that receive the distal ends of arms 170a and 170b, such distal ends being flared to prevent disengagement from fasteners 135. Of course, other fastening mechanisms well-known to one of skill in the art can be used to secure distal ends of arms 170a and 170b to lead body 70. For example, fasteners 135 can comprise male fasteners and the distal ends of arms 170 can have female fasteners attached thereto or integral therewith that act in cooperation with the male fasteners of lead body 70 to secure installation tool 130 to lead body 70. Referring further to FIG. 10, installation tool 130 may further comprise a second pivot 190 located proximal to first pivot 180 connecting arms 170a and 170b.

The present invention also provides a corpus callosum neuromodulation system including neuromodulation assembly 60 and further including components useful in identifying, monitoring, or affecting a target region of the corpus callosum 10. For example, such a system could include a component for lesioning and temperature monitoring, and/or a component that has a fiberoptic monitor which allows telemetric intracranial monitoring capabilities, and/or a microelectrode recording component, and/or a sensing component to incorporate a feedback mechanism to assist in determining whether lead body 70 should be adjusted. With respect to a sensing component, referring to FIG. 14, a sensor 550 can be incorporated with the corpus callosum electrical stimulation system according to the present invention. Sensor 550 can be used with a closed-loop feedback system in order to automatically determine the level of stimulation necessary to provide the desired therapy. Sensor 550 may be implanted into a portion of a patient P's body suitable for detecting characteristics, symptoms or attributes of the condition or disorder being treated such as electrical brain activity, cerebral blood flow, and/or vital signs or other chemical and electrical activity of the body. Sensors suitable for use in a system according to the present invention include, for example, those disclosed in U.S. Pat. No. 5,711,316, which is incorporated by reference herein. In cases where the attribute of the symptom is the electrical activity of the brain, stimulating electrodes may be intermittently used to record electrical activity. Alternatively, one or more electrodes implanted within the brain may serve as a sensor or a recording electrode. When necessary, these sensing or recording electrodes may deliver stimulation therapy to the target region of the corpus callosum. The output of an external feedback sensor may communicate with an implanted pulse generator through a telemetry down-link. Any sensing functions in accordance with the present invention can be performed locally, distally, or remotely from the target site and the present invention also contemplates use of neuromodulation assembly 60 integration with imaging methods known in the art such as X-rays, computer tomography, magnetic resonance imaging, and functional magnetic resonance imaging.

In an exemplary method of using an neuromodulation assembly 60 of the present invention, a patient is positioned on the operating table in the supine position under general endotracheal anesthesia. The patient's head is immobilized using a pin head holder. An incision is made on skin of the skull, in one of several fashions: frontotemporal, bifrontal, frontal, frontotemporoparietal or other. After the skip flap is retracted, a frontal-parietal craniotomy is performed passing the midline to expose the superior sagital sinus. Alternatively, other craniotomies can also be made, such as a bifrontal craniotomy, frontotemporo craniotomy, frontotemporoparietal craniotomy, craniotomies extended to the controlateral side and other variations. The dura mater is tacked to the skull and opened in an arc with the dura mater's base toward the midline. Dissection is continued until the interhemispheric fissure is adequately exposed at the level of the falx. The interhemispheric fissure is dissected using microneurosurgical techniques known to one of skill in the art. The interhemispheric fissure is dissected until the corpus callosum is adequately exposed. The branches of the anterior communicating artery may be dissected away to create necessary area to implant an neuromodulation assembly 60 of the present invention.

Neuromodulation assembly 60 is then delivered to the surface of corpus callosum 10 by any appropriate method known in the art. For example, as illustrated in FIG. 10, an installation tool may be used which grips and folds lead body 70 into the pre-operative position and then delivers and places lead body 70 in the operative position on the target region of the corpus callosum 10.

Figure 11:
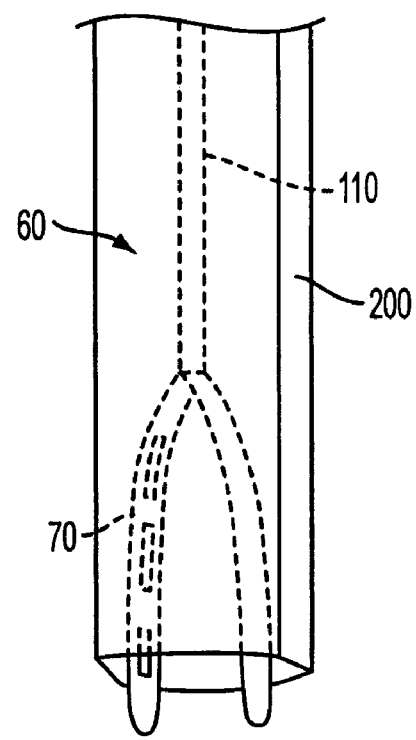
FIG. 11 depicts a neuromodulation assembly of the present invention wherein the lead body is in a pre-operative position inside a cannula.
Figure 12:
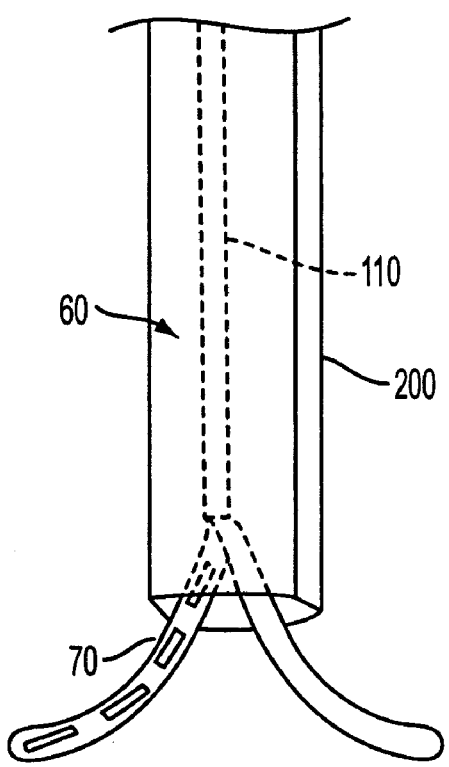
FIG. 12 depicts the neuromodulation assembly of FIG. 11 wherein the lead body is shown exiting the distal end of the cannula.

Referring to FIG. 11, neuromodulation assembly 60 may also be delivered to the corpus callosum 10 via a cannula 200. In such a case, lead body 70 is folded and inserted into cannula 200 and delivered to the corpus callosum 10. Referring to FIG. 12, as lead body 70 exits the distal end of cannula 200, lead body 70 unfolds and can assume the operative position on the corpus callosum 10. To assist in preventing unnecessary lateral movement or rotation of lead body 70 as it travels down cannula 200 and exits the distal end thereof, cannula 200 may include a guide from which lead body 70 depends, or tracks that direct lead body 70 in an outwardly direction away from cannula 200, when lead body 70 is advanced out of the distal end of cannula 200.

Figure 15:
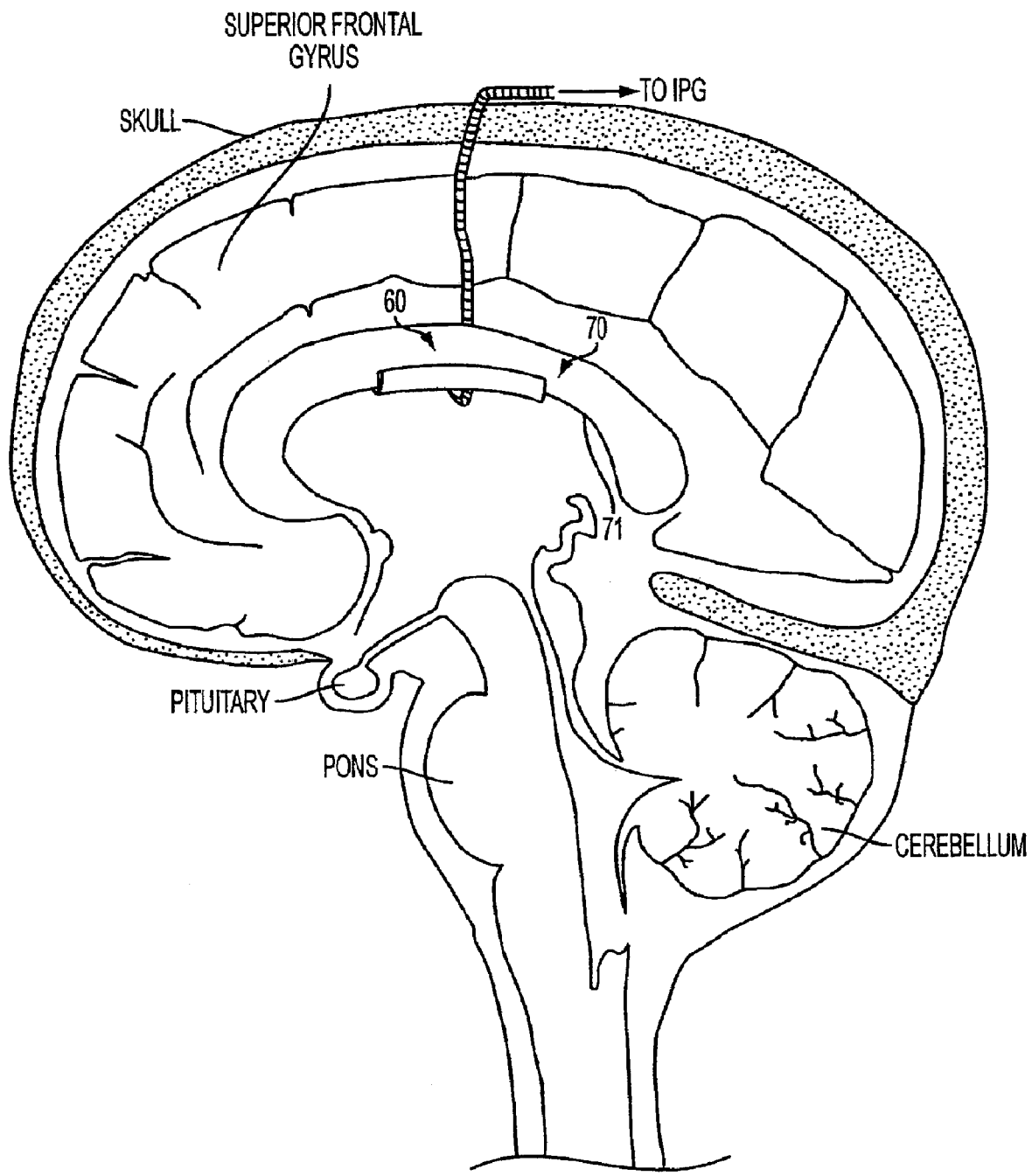
FIG. 15 depicts a neuromodulation assembly wherein the lead body is on the bottom surface of the trunk of the corpus callosum.

Of course, other methods of delivering and implanting neuromodulation assembly 60, including using conventional neurosurgical instrumentation, are within the knowledge of one of skill in the art and the neuromodulation assembly 60 is not limited to delivery by any particular method. For example, lead body 70 can be delivered by any minimally invasive technique such as endoscopically and/or intravascularly. Referring to FIG. 15, neuromodulation assembly 60 can be delivered to the target region of the corpus callosum, such as the trunk 40, neuroendoscopically through the lateral ventricle such that lead body 70 is in contact with the under surface 71 of the trunk 40 of the corpus callosum 10.

Once lead body 70 is placed on the target region of the corpus callosum 10, neuromodulation assembly 60 is anchored in the brain by securing anchor 115 to the dura mater of the falx and/or the dura mater of the convexity, for example. Closure of the craniotomy can be performed using standard methods well-known to one of skill in the art. A tunneling device can then be used to dissect a subcutaneous tunnel down to the subclavicular level, where a subcutaneous pocket can be made to accommodate an implantable pulse generator. An extension wire can then be passed through the tunnel to connect the neuromodulation assembly to the pulse generator. Alternatively, other sites can be used for implantation of the pulse generator, such as the abdominal wall and the lower back area below the posterior iliac crest.

After implantation, the electrodes of lead body 70 may be adjusted post-operatively by turning them on or off, adjusting the voltage, adjusting the frequency, and adjusting other electrical signal parameters through the use of telemetry, RF signals, or other systems known in the art. Those skilled in the art will appreciate that electrical properties of the electrodes and the resulting electrical field may be varied by selectively powering individual or groups of electrodes formed from or controlled by micro-electrical mechanical systems (MEMS). Moreover, MEMS actuators may drive electrodes, drug delivery catheters, sensing probes, and the like from the cannula to desired locations in an area of interest.

Neuromodulation assembly 60 may also be implemented within a drug delivery system to provide chemical stimulation utilizing a drug, pharmaceutical, or therapeutic agent. In this embodiment, the signal generator is replaced with or includes a pump and the electrodes are replaced with a catheter or drug ports. The pump may be implanted below the skin of a patient and has a port into which a hypodermic needle can be inserted through the skin to inject a quantity of a liquid, such as a drug, pharmaceutical, or therapeutic agent. The liquid agent is delivered from a pump through a catheter port into a catheter. The catheter is positioned to deliver the liquid agent to specific infusion sites in the brain. Alternatively, neuromodulation assembly 60 may be combined with a drug delivery system to provide both chemical and electrical modulation to target regions of the corpus callosum.

Figure 13:
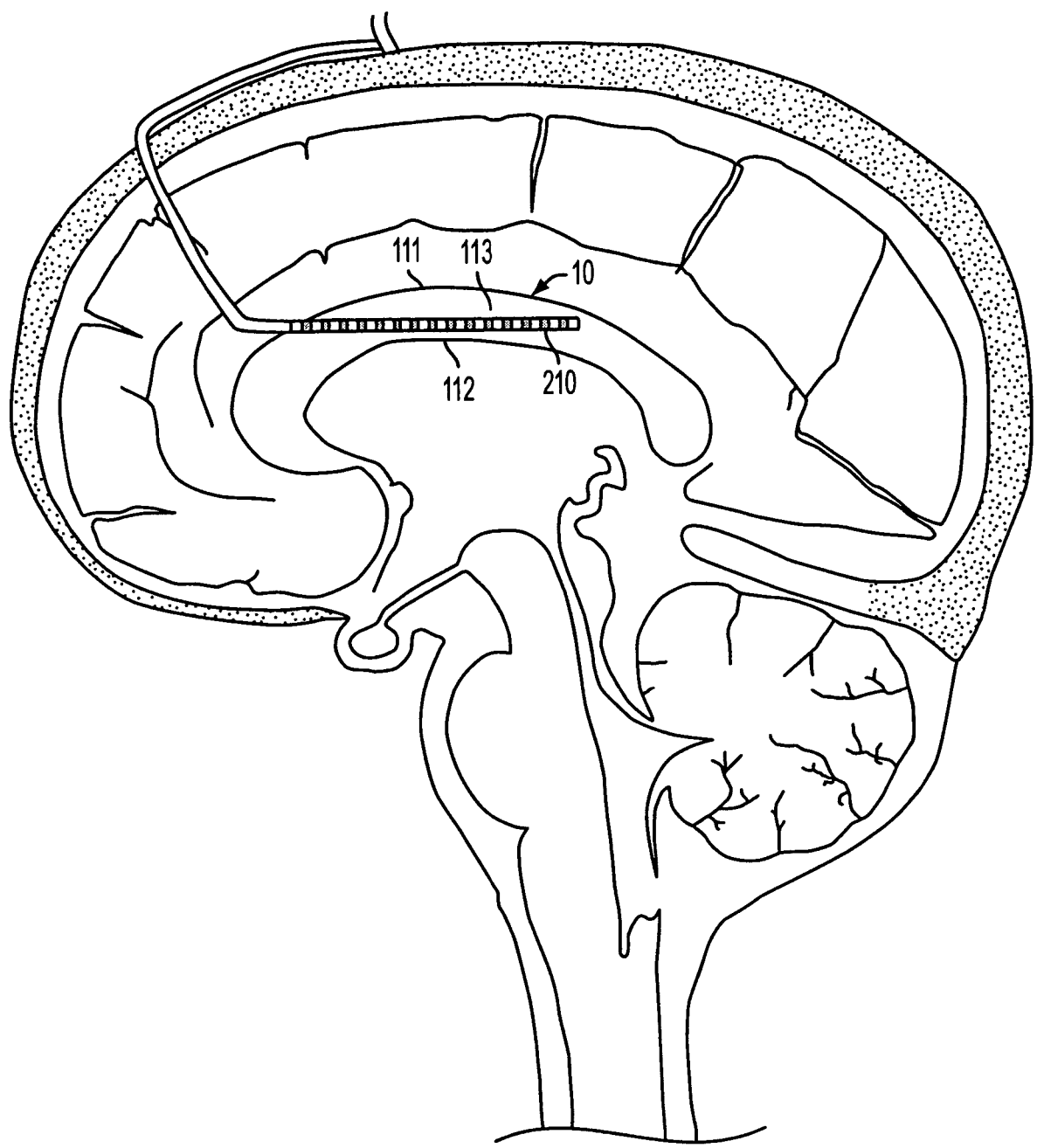
FIG. 13 is a sagittal section of the brain illustrating a cylindrical lead that is positioned within the corpus callosum along the longitudinal axis thereof.

In another embodiment, the present invention provides a method of stimulating the corpus callosum 10 by placing an electrode lead having an electrode disposed thereon and preferably a plurality of electrodes, in communication with the corpus callosum 10. The method further comprises activating the electrode to apply an electrical signal to the corpus callosum 10 to stimulate the corpus callosum 10. Referring to FIG. 13, the electrical lead can penetrate the thickness 113 of the corpus callosum along the longitudinal axis thereof. Alternatively, the electrical lead can be placed on the top surface 111 or the bottom surface 112 of the corpus callosum. The electrical lead, according to this method, may be any electrical lead that is configured to stimulate the corpus callosum. For example, the electrical lead can be neuromodulation assembly 70 according to the present invention or any other suitable lead, such as a cylindrical lead 210, as illustrated in FIG. 13, which penetrates the corpus callosum 10 along the longitudinal axis thereof. In such an embodiment, cylindrical lead 210 having an electrode, and preferably a plurality of electrodes, disposed thereon can be inserted in the brain and into the corpus callosum through a cannula guided by a stereotactic apparatus. A conductor coupled to electrical contact and extending from lead 210 can be anchored to the skull via a burr hole anchoring device. Alternatively, cylindrical lead 210 can be anchored to dura mater, as described above with respect to neuromodulation assembly 60.

In another embodiment, the present invention provides a method of securing in the brain an electrical lead comprising a lead body having an electrode, and preferably a plurality of electrodes, disposed thereon. The method comprises anchoring the electrical lead to the dura mater of the brain, such as the dura mater of the convexity or the falx. Such an anchoring method may be a preferred method of anchoring an electrical lead in electrical neuromodulation procedures where the lead is positioned on the surface of the target site rather than penetrating the target site. For example, such a method may be used to anchor devices that stimulate structures in the brain that are located in cisterns, such as the basal cisterns, or superficial structures, such as the surface of the cerebellum, or the sylvian fissure.

The foregoing description and examples have been set forth merely to illustrate the invention and are not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

We claim:

1. A neuromodulation assembly comprising:
    a lead body having a top surface and a bottom surface, the lead body is configured to retain a pre-set curvature that mimics the curvature of the trunk, genu, splenium, or rostrum of the corpus callosum in an operative position of the lead body;
    an electrical contact exposed at the bottom surface and not the top surface of the lead body;
    a conductor coupled to the electrical contact and extending from the lead body; and
    an anchor disposed on the conductor.

2. The neuromodulation assembly of claim 1, wherein the lead body retains a pre-set curvature that mimics the curvature of the trunk of the corpus callosum in the operative position of the lead body.

3. The neuromodulation assembly of claim 2, wherein the conductor extends from substantially the center of the lead body.

4. The neuromodulation assembly of claim 1, wherein the lead body retains a pre-set curvature that mimics the curvature of the rostrum of the corpus callosum in the operative position of the lead body.

5. The neuromodulation assembly of claim 1, wherein the lead body retains a pre-set curvature that mimics the curvature of the splenium of the corpus callosum in the operative position of the lead body.

6. The neuromodulation assembly of claim 1, wherein the lead body retains a pre-set curvature that mimics the curvature of the genu of the corpus callosum in the operative position of the lead body.

7. The neuromodulation assembly of claim 1, wherein the lead body is fabricated from a flexible material and is deformable from a pre-operative position to the operative position.

8. The neuromodulation assembly of claim 7, wherein the material is a shape memory alloy.

9. The neuromodulation assembly of claim 1, wherein the anchor comprises a plurality of anchors.

10. The neuromodulation assembly of claim 1, wherein the anchor is selected from the group consisting of: a tine, a hook, and a suture sleeve.

11. The neuromodulation assembly of claim 1, wherein the anchor is slidably disposed on the conductor.

12. The neuromodulation assembly of claim 1, wherein the lead body further comprises a fastener.

13. The neuromodulation assembly of claim 12, wherein the fastener comprises a pair of fasteners.

14. An electrical stimulation kit comprising the neuromodulation assembly of claim 13, and further comprising an installation tool having a proximal portion comprising a handle and a distal portion comprising a pair of arms that are connected by a first pivot, the pair of arms having distal ends configured to releasably cooperate with the pair of fasteners of the lead body.

15. The electrical stimulation kit of claim 14, wherein the installation tool further comprises a second pivot connecting the pair of arms, the second pivot located proximal to the first pivot.

16. The electrical stimulation kit of claim 14, wherein the pair of fasteners of the lead body comprise male fasteners and the distal ends of the pair of arms comprise female fasteners, the male and female fasteners acting in cooperation with each other to secure the installation tool to the lead body.

17. The neuromodulation assembly of claim 12, wherein the fastener comprises a male fastener for cooperation with a female fastener.

18. The neuromodulation assembly of claim 12, wherein the fastener comprises a strap, a groove, a buckle, a through-hole, or a snap.

19. The electrical lead of claim 1, wherein the electrical contact comprises a plurality of electrical contacts.

20. The neuromodulation assembly of claim 1, wherein the lead body has a J-shaped curvature in the operative position of the lead body.

21. The neuromodulation assembly of claim 1, wherein the lead body has a cambered curvature in the operative position of the lead body.

22. A neuromodulation assembly comprising:
    a lead body having a top surface and a bottom surface, the lead body having a curvature that mimics the curvature of the trunk, genu, splenium, or rostrum of the corpus callosum in an operative position of the lead body;
    an electrical contact exposed at the bottom surface and not the top surface of the lead body;
    a fastener on the lead body for receiving an installation tool;
    a conductor coupled to the electrical contact and extending from the lead body; and
    an anchor disposed on the conductor.

23. A neuromodulation assembly comprising:
    a lead body having a top surface and a bottom surface, the lead body having a curvature that mimics the curvature of the trunk, genu, splenium, or rostrum of the corpus callosum in an operative position of the lead body;
    an electrical contact exposed at the bottom surface and not the top surface of the lead body;
    a conductor coupled to the electrical contact and extending from the lead body;
    an anchor disposed on the conductor; and
    a pulse generator programmed to stimulate a region of the corpus callosum.

24. A method of stimulating a corpus callosum, the method comprising:
    placing the neuromodulation assembly of claim 1 in communication with a corpus callosum; and
    activating the electrical contact to apply an electrical signal to the corpus callosum to stimulate the corpus callosum.

25. The method of claim 24, wherein the electrical contact comprises a plurality of electrical contacts.

26. The method of claim 24, wherein the lead body of the neuromodulation assembly is delivered to the corpus callosum intravascularly.

27. The method of claim 24, wherein the corpus callosum has an under-surface and the lead body is placed on the under-surface of the corpus callosum.

* * * * *